United States Patent [19]

Weeks

[11] Patent Number: Plant 5,828

[45] Date of Patent: Dec. 16, 1986

[54] ROSE PLANT

[76] Inventor: O. L. Weeks, 926 W. Philadelphia, Ontario, Calif. 91761

[21] Appl. No.: 698,221

[22] Filed: Feb. 4, 1985

[51] Int. Cl.[4] ..... A01H 5/00

[52] U.S. Cl. ..... Plt./12

[58] Field of Search ..... Plt./12

*Primary Examiner*—Robert E. Bagwill

*Attorney, Agent, or Firm*—Vincent G. Gioia

[57] ABSTRACT

A new grandiflora rose variety of Spinel red and Naples yellow bicoloring.

1 Drawing Figure

The present invention relates to a new and distinct variety of rose plant of the grandiflora rose class, which was originated by my crossing as seed parent the rose known as "Bob Hope" (U.S. Plant Pat. No. 2,734) and an unpatented, unnamed seedling of my creation as pollen parent. The denomination of this new variety is "Risque".

Among the novel characteristics possessed by this new variety which distinguish it from it parents and all other varieties of which I am aware are its flowers of Spinel red and Naples yellow bicoloring unusual in a grandiflora rose. Buds are high centered and show bicoloring best before bloom becomes fully open. Flowers are attractively formed and borne on strong stems making the variety useful both as a garden plant and as a cut flower. Asexual reproduction by budding of the new variety as performed in San Bernardino County, Calif., shows that the foregoing and other distinguishing characteristics come true to form and are established and transmitted through succeeding propagations.

The accompanying drawing shows typical specimens of the vegetative growth and flowers of the new variety in different stages of development and as depicted in color as nearly true as it is reasonably possible to make the same in a color illustration of this character.

The following is a detailed description of my new variety, with color terminology in accordance with The Royal Horticultural Society Colour Chart (R.H.S.C.C.). The terminology used in color description herein refers to plate numbers in the aforementioned color chart, e.g., "54A" is plate 54A of The Royal Horticultural Society Colour Chart.

Parentage: Seedling.

*Seed parent.*—"Bob Hope".

*Pollen parent.*—Unnamed seedling.

Class: Grandiflora.

The following observations are made of specimens grown outdoors in San Bernardino County, Calif., during the month of October.

FLOWER

Blooming habit: Recurrent.

A. Bud:

(1) *Size.*—Medium.

(2) *Form.*—Short pointed.

(3) *Color.*—As sepals separate, bud appears spinel red with yellow striping with more significant yellow coloring at point of petal attachment.

After sepals fall, distinct different colors of petal top and undersurfaces become quickly evident.

(4) *Sepals.*—Short, same length as bud, few fancy and few smooth.

(5) *Peduncle.*—Length — long, with small prickles. Aspect — straight. Strength — erect, strong. Color — near 147C, with reddish purple cast.

B. Bloom:

(1) *Size.*—Average size when fully expanded — about 4 inches.

(2) *Borne.*—Singly and several together in sprays.

(3) *Form.*—High centered, petals reflex upon opening, outer petals quill to points, other petals roll loosely outward.

(4) *Petalage.*—Number of petals under normal conditions — about 25 to 28.

(5) *Color.*—After sepals fall, high centered bud to $\frac{1}{3}$ open stage displays sharp color contrast between spinel red, near 54A, petal top surface and Naples yellow, near 11A, petal undersurface. Coloring of petal top surface tends to be substantial, uniform, and stays the same as flower matures, but lightens somewhat as blooms age. Color of petal undersurface tends not to be uniform with Naples yellow tonality deepening at lower segments of petals and spinel red washing into the Naples yellow coloring at upper segments of the petals. Aged open blooms tend to show some bluing with overall color tending toward near 66C and D and yellow coloring showing only at flower center.

C. Petals:

(1) *Texture.*—Medium thick.

(2) *Appearance.*—Crepe-like appearance outside, inside satiny.

(3) *Form.*—Ovate.

(4) *Arrangement.*—Regular.

(5) *Petaloids in center.*—5 to 6.

(6) *Persistence.*—Drop off cleanly.

(7) *Fragrance.*—None.

(8) *Lasting quality.*—Long lasting on plant and as cut flower.

REPRODUCTIVE ORGANS

A. Stamens, filaments and anthers:

*Arrangement.*—Irregularly arranged around styles, sparse.

B. Pollen: Color — light yellow.

C. Styles: Uneven, short to medium length.

D. Stigmas: Color — Yellow.

E. Hips: None observed.

PLANT

A. Form: Upright, tall, compact.
B. Growth: Very vigorous, uniform branching.
*Height attained.*—about 4 to 4½ feet.
C. Foliage: Compound 5 leaflets.
(1) *Size.*—Medium.
(2) *Quantity.*—Abundant.
(3) *Color.*—New foliage: Upper side — reddish purple. Under side — reddish purple. Old foliage: Upper side — near 147A. Under side — near 147B.
(4) *Shape.*—Oval, pointed.
(5) *Texture.*—Upper side is leathery and under side is dull.
(6) *Edge.*—Serrated.
(7) *Serration.*—Simple.
(8) *Leaf stem.*—Color — near to 147C. Under side — near 147C.
(9) *Stipules.*—Short to medium.

(10) *Resistance to disease.*—Average.
D. Wood:
(1) *New wood.*—Color — reddish purple. Bark — smooth.
(2) *Old wood.*—Color — near 148A to B. Bark — smooth.
E. Thorne:
(1) *Thorns.*—Quantity (main stalk) — very few, flat, pointed down, reddish brown.
(2) *Prickles.*—Small, few.
F. Winter hardiness: Needs winter protection in severe climates.

I claim:

1. A new and distinct variety of rose plant of the grandiflora rose class, substantially as shown and described, characterized particularly by unique Spinel red and Naples yellow bicolor flowers with red petal top surface and yellow petal undersurface.

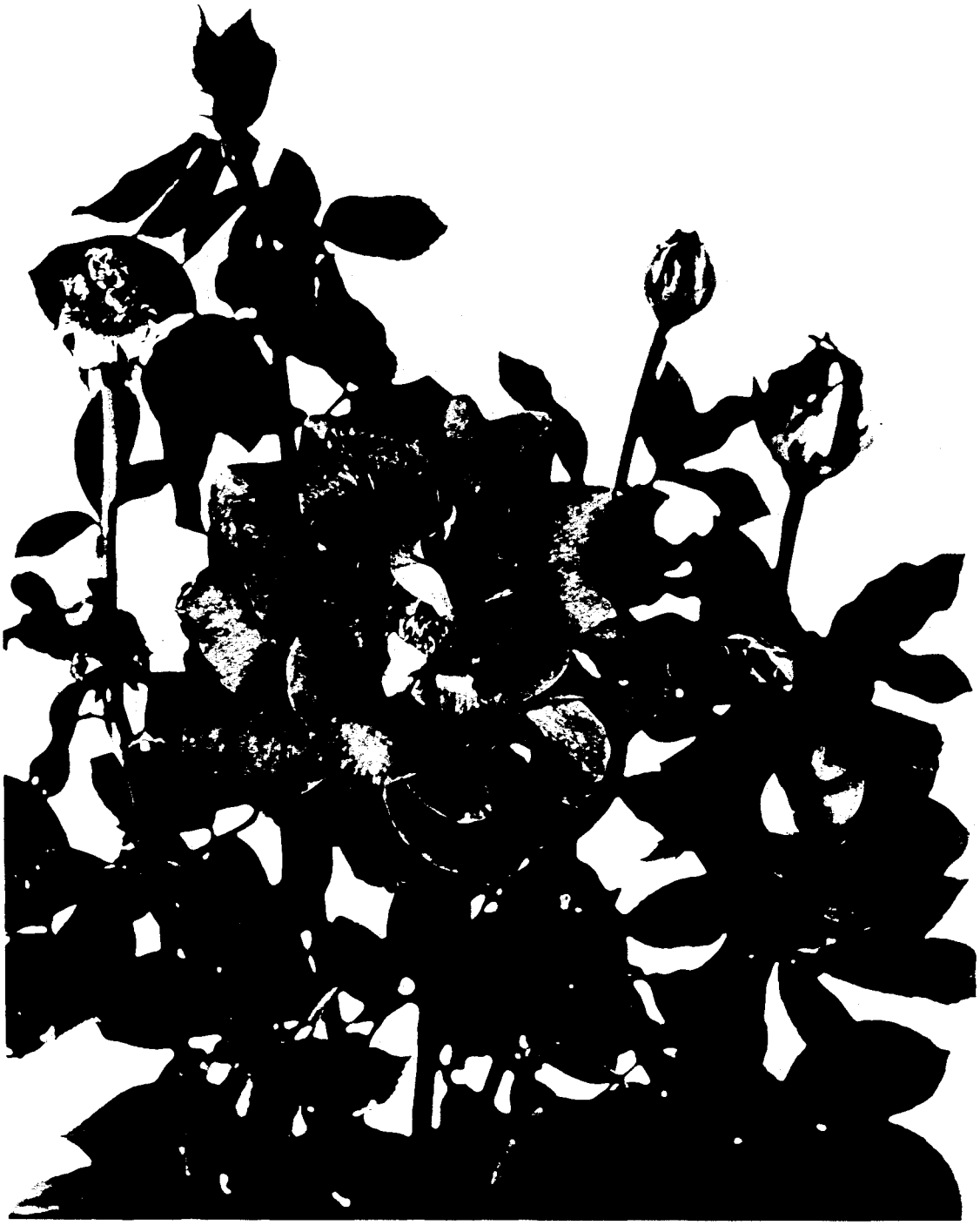

* * * * *